United States Patent
Dong et al.

(10) Patent No.: US 10,544,174 B2
(45) Date of Patent: Jan. 28, 2020

(54) PROCESS FOR THE ALKOXYCARBONYLATION OF ETHYLENICALLY UNSATURATED COMPOUNDS WITH MONOPHOSPHINE LIGANDS

(71) Applicant: EVONIK DEGUSSA GMBH, Essen (DE)

(72) Inventors: Kaiwu Dong, Bo Zhou (CN); Ralph Jackstell, Cuxhaven Altenwalde (DE); Matthias Beller, Ostseebad Nienhagen (DE); Dirk Fridag, Haltern am See (DE); Dieter Hess, Marl (DE); Katrin Marie Dyballa, Recklinghausen (DE); Frank Geilen, Haltern am See (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 65 days.

(21) Appl. No.: 15/649,743

(22) Filed: Jul. 14, 2017

(65) Prior Publication Data
US 2018/0022764 A1 Jan. 25, 2018

(30) Foreign Application Priority Data
Jul. 19, 2016 (EP) ..................................... 16180050

(51) Int. Cl.
C07F 9/50 (2006.01)
C07C 67/38 (2006.01)
(Continued)

(52) U.S. Cl.
CPC ............ C07F 9/5045 (2013.01); C07C 67/38 (2013.01); C07F 15/0066 (2013.01); C07D 403/14 (2013.01); C07D 405/14 (2013.01)

(58) Field of Classification Search
None
See application file for complete search history.

(56) References Cited

U.S. PATENT DOCUMENTS 4,786,443 A 11/1988 Drent et al.
5,028,576 A 7/1991 Drent et al.
(Continued)

FOREIGN PATENT DOCUMENTS

CN 101857608 A 10/2010
DE 10322408 A1 12/2004
(Continued)

OTHER PUBLICATIONS

Fang et al. (Angew. Chem., Int. Ed., 53, 9030-9034), (Year: 2014).*
Beller et al. (ChemCatChem, 1, 28-41 (Year: 2009).*

U.S. Appl. No. 15/649,759, Dong, et al., filed Jul. 14, 2017.
U.S. Appl. No. 15/649,770, Dong, et al., filed Jul. 14, 2017.
U.S. Appl. No. 15/649,781, Dong, et al., filed Jul. 14, 2017.
U.S. Appl. No. 15/651,042, Fang, et al., filed Jul. 17, 2017.
U.S. Appl. No. 15/651,105, Dong, et al., filed Jul. 17, 2017.
U.S. Appl. No. 15/651,169, Dong, et al., filed Jul. 17, 2017.
U.S. Appl. No. 15/651,062, Dong, et al., filed Jul. 17, 2017.
(Continued)

Primary Examiner — Yun Qian
(74) Attorney, Agent, or Firm — Smith, Gambrell & Russell, LLP

(57) ABSTRACT

The invention relates to a process comprising the following process steps:

a) introducing an ethylenically unsaturated compound;
b) adding a monophosphine ligand and a compound which comprises Pd, or adding a complex comprising Pd and a monophosphine ligand;
c) adding an aliphatic alcohol;
d) supplying CO;
e) heating the reaction mixture, the ethylenically unsaturated compound being reacted to form an ester;

where the monophosphine ligand is a compound of formula (I)

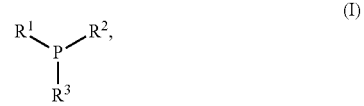

where
$R^1$ is selected from —$(C_1$-$C_{12})$-alkyl, —O—$(C_1$-$C_{12})$-alkyl, —O—$(C_6$-$C_{20})$-aryl, —$(C_6$-$C_{20})$-aryl, —$(C_3$-$C_{12})$-cycloalkyl, —$(C_3$-$C_{12})$-heterocycloalkyl, —$(C_3$-$C_{20})$-heteroaryl;

$R^2$ is selected from —$(C_6$-$C_{20})$-aryl, —$(C_3$-$C_{12})$-cycloalkyl, —$(C_3$-$C_{12})$-heterocycloalkyl, —$(C_3$-$C_{20})$-heteroaryl;

$R^3$ is —$(C_3$-$C_{20})$-heteroaryl;

and $R^1$, $R^2$ and $R^3$ may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, halogen.

5 Claims, No Drawings

(51) Int. Cl.
  *C07F 15/00* (2006.01)
  *C07D 403/14* (2006.01)
  *C07D 405/14* (2006.01)

(56) References Cited

U.S. PATENT DOCUMENTS

| | | | |
|---|---|---|---|
| 5,124,300 | A | 6/1992 | Drent et al. |
| 7,589,082 | B2 | 9/2009 | Zapf et al. |
| 2017/0022137 | A1 | 1/2017 | Dong et al. |
| 2017/0022138 | A1 | 1/2017 | Dong et al. |
| 2017/0022139 | A1 | 1/2017 | Dong et al. |
| 2017/0022234 | A1 | 1/2017 | Jennerjahn et al. |
| 2017/0022235 | A1 | 1/2017 | Dong et al. |
| 2017/0022236 | A1 | 1/2017 | Dong et al. |

FOREIGN PATENT DOCUMENTS

| | | |
|---|---|---|
| EP | 0 282 142 A2 | 9/1988 |
| EP | 0 441 446 A1 | 8/1991 |
| JP | S63-238036 A | 10/1988 |
| JP | H04-215852 A | 8/1992 |
| JP | H08-299803 A | 11/1996 |
| JP | 2008-247745 A | 10/2008 |
| WO | 97/17320 | 5/1997 |
| WO | 2011/083305 A1 | 7/2011 |

OTHER PUBLICATIONS

European Search Report dated Jan. 5, 2017 for EP 16 18 0050 (1 page).

Liu, J., et al. Ligand-Controlled Palladium-Catalyzed Alkoxycarbonylation of Allenes: Regioselective Synthesis of α, β,- and β, γ-Unsaturated Esters. Journal of the American Chemical Society, vol. 137, Nr. 26, 2015, pp. 8556-8563.

Brennfuhrer A. et al. Palladium-Catalyzed Carbonylation Reaction of Alkenes and Alkynes. ChemCatChem, vol. 1, Nr. 1, 2009, pp. 28-41.

Rataboul, F, et al. New Ligands for a General Palladium-Catalyzed Amination of Aryl and Heteroaryl Chlorides. Chem. Eur. J, 2004, vol. 10, pp. 2983-2990.

European Office Communication dated Sep. 18, 2018 for European Patent Application No. 16180050.3 (4 pages in German with English machine translation).

Japanese Office Action dated Aug. 30, 2018 for Japanese Patent Application No. 2017-137954 (4 pages in Japanese with English machine translation).

Khokarale, S. et al. Zwitterion enhanced performance in palladium-phosphine catalyzed ethylene methoxycarbonylation, Catalysis Communications, 2014, vol. 44, pp. 73-75.

Fang, X et al. Palladium-Catalyzed Alkoxycarbonylation of Conjugated Dienes under Acid-Free Conditions: Atom-Economic Synthesis of β, γ-Unsaturated Esters, Agnew Chem. Int. Ed, 2014, pp. 9030-9034.

Armarego, W. et al. Purification of Laboratory Chemicals, Butterworth Heinemann (Elsevier), 6th edition, Oxford 2009 (index and chapter abstracts provided).

Harris, R. et al. NMR Nomenclature, Nuclear Spin Properties and Conventions for Chemical Shifts, Pure Appl. Chem., 2001, No. 73, pp. 1795-1818.

Harris, R. et al. Further Conventions for NMR Shielding and Chemical Shifts. Pure Appl. Chem., 2008, No. 80, pp. 59-84.

Köppe, R. et al. Quntenchemische und Experimentelle Untersuchungen zur Stabilität und Struktur von $GaAs_5$ und $InAs_5$. Angew. Chem. 2004, No. 116, pp. 2222-2225.

Budzelaar, P. et al. Synthesis and Coordination Chemistry of a New Class of Binucleating Ligands: Pyridyl-Substituted Diphosphines. Organometallics 1990, No. 9, pp. 1222-1227.

Malaysian Search Report dated Jul. 4, 2019 for MY Patent App No. PI2017702598 (1 page).

Examination Report of the Patent office of the Cooperation Council for the Arab States of the Gulf dated Jun. 30, 2019 for Patent App No. GC 2017-337711 (5 pages).

* cited by examiner

PROCESS FOR THE ALKOXYCARBONYLATION OF ETHYLENICALLY UNSATURATED COMPOUNDS WITH MONOPHOSPHINE LIGANDS

The present invention relates to a novel process for the alkoxycarbonylation of ethylenically unsaturated compounds with monophosphine ligands.

The alkoxycarbonylation of ethylenically unsaturated compounds is a process of increasing significance. An alkoxycarbonylation is understood to mean the reaction of ethylenically unsaturated compounds, such as olefins, with carbon monoxide and alcohols in the presence of a metal or of a metal complex and of a ligand to give the corresponding esters:

Scheme 1: General reaction equation of the alkoxycarbonylation of an ethylenically unsaturated compound

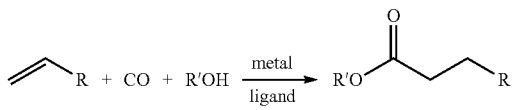

Among the alkoxycarbonylation reactions, the ethene methoxycarbonylation to give 3-methyl-propionate is of significance as an intermediate stage for the preparation of methyl methacrylate (S. G. Khokarale, E. J. García-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

The alkoxycarbonylation may lead to branched (iso) or linear (n) products. Besides the yield, therefore, the n/iso selectivity is an important parameter in the development of new catalytic systems for alkoxycarbonylation.

Using monophosphine compounds as ligands for the alkoxycarbonylation is known. One example of this is the alkoxycarbonylation of isoprene with benzyl alcohol in the presence of a Pd complex. In this reaction, for example, good yields have been achieved using the ligand N-phenyl-2-(di-tert-butylphosphino)pyrrole, which is available under the trade name cataCXium PtB (Fang X. et al., Angew. Chem. Int. Ed., 2014, 53, 9030-9034). However, the selectivity achieved by this ligand is low. Similar heteroaryl-substituted monophosphine compounds, specifically N-phenyl-2-(di-phenylphosphino)pyrrole and N-phenyl-2-(di-cyclohexylphosphino)pyrrole, have likewise been studied, but achieve only low yields in the alkoxycarbonylation of isoprene with benzyl alcohol (Fang X. et al., loc. cit.). The reaction of isoprene with aliphatic alcohols has not been studied.

The problem addressed by the present invention is that of providing a novel process for the alkoxycarbonylation of ethylenically unsaturated compounds with monophosphine ligands, with which a high yield and high n/iso selectivity can be achieved. More particularly, the process is to be suitable for the alkoxycarbonylation of long-chain ethylenically unsaturated compounds, for example $C_8$ olefins.

This problem is solved by a process comprising the following process steps:

a) introducing an ethylenically unsaturated compound;
b) adding a monophosphine ligand and a compound which comprises Pd, or adding a complex comprising Pd and a monophosphine ligand;
c) adding an aliphatic alcohol;
d) supplying CO;
e) heating the reaction mixture, the ethylenically unsaturated compound being reacted to form an ester;

where the monophosphine ligand is a compound of formula (I)

where
$R^1$ is selected from —$(C_1$-$C_{12})$-alkyl, —O—$(C_1$-$C_{12})$-alkyl, —O—$(C_6$-$C_{20})$-aryl, —$(C_6$-$C_{20})$-aryl, —$(C_3$-$C_{12})$-cycloalkyl, —$(C_3$-$C_{12})$-heterocycloalkyl, —$(C_3$-$C_{20})$-heteroaryl;
$R^2$ is selected from —$(C_6$-$C_{20})$-aryl, —$(C_3$-$C_{12})$-cycloalkyl, —$(C_3$-$C_{12})$-heterocycloalkyl, —$(C_3$-$C_{20})$-heteroaryl;
$R^3$ is —$(C_3$-$C_{20})$-heteroaryl;
and $R^1$, $R^2$ and $R^3$ may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —SO$_3$H, —NH$_2$, halogen.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in two or more steps, in such a way that, for example, a portion of the CO is first fed in, then the mixture is heated, and then a further portion of the CO is fed in.

The expression $(C_1$-$C_{12})$-alkyl encompasses straight-chain and branched alkyl groups having 1 to 12 carbon atoms. These are preferably $(C_1$-$C_8)$-alkyl groups, more preferably $(C_1$-$C_6)$-alkyl, most preferably $(C_1$-$C_4)$-alkyl.

Suitable $(C_1$-$C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-timethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1$-$C_{12})$-alkyl also apply particularly to the alkyl groups in —O—$(C_1$-$C_{12})$-alkyl, —S—$(C_1$-$C_{12})$-alkyl, —COO—$(C_1$-$C_{12})$-alkyl, —CONH—$(C_1$-$C_{12})$-alkyl, —CO—$(C_1$-$C_{12})$-alkyl and —N—[$(C_1$-$C_{12})$-alkyl]$_2$.

The expression $(C_3\text{-}C_{12})$-cycloalkyl encompasses mono-, bi- or tricyclic hydrocarbyl groups having 3 to 12 carbon atoms. Preferably, these groups are $(C_5\text{-}C_{12})$-cycloalkyl.

The $(C_3\text{-}C_{12})$-cycloalkyl groups have preferably 3 to 8, more preferably 5 or 6, ring atoms.

Suitable $(C_3\text{-}C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3\text{-}C_{12})$-cycloalkyl also apply particularly to the cycloalkyl groups in —O—$(C_3\text{-}C_{12})$-cycloalkyl, —S—$(C_3\text{-}C_{12})$-cycloalkyl, —COO—$(C_3\text{-}C_{12})$-cycloalkyl, —CONH—$(C_3\text{-}C_{12})$-cycloalkyl, —CO—$(C_3\text{-}C_{12})$-cycloalkyl.

The expression $(C_3\text{-}C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3\text{-}C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3\text{-}C_{12})$-heterocycloalkyl group in the context of this invention is thus also ethylene oxide.

Suitable $(C_3\text{-}C_{12})$-heterocycloalkyl groups are especially tetrahydrothiophenyl, tetrahydrofuryl, tetrahydropyranyl and dioxanyl.

The expression $(C_6\text{-}C_{20})$-aryl encompasses mono- or polycyclic aromatic hydrocarbyl radicals having 6 to 20 carbon atoms. These are preferably $(C_6\text{-}C_{14})$-aryl, more preferably $(C_6\text{-}C_{10})$-aryl.

Suitable $(C_6\text{-}C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6\text{-}C_{20})$-aryl groups are phenyl, naphthyl and anthracenyl.

The expressions $(C_6\text{-}C_{20})$-aryl-$(C_1\text{-}C_{12})$-alkyl and $(C_6\text{-}C_{20})$-aryl-O—$(C_1\text{-}C_{12})$-alkyl encompass $(C_6\text{-}C_{20})$-aryl groups substituted by a —$(C_1\text{-}C_{12})$-alkyl or —O—$(C_1\text{-}C_{12})$-alkyl group, respectively.

Suitable $(C_6\text{-}C_{20})$-aryl-$(C_1\text{-}C_{12})$-alkyl groups are, for example, tolyl groups, especially o-tolyl. An example of a suitable $(C_6\text{-}C_{20})$-aryl-O—$(C_1\text{-}C_{12})$-alkyl group is 2-methoxyphenyl.

The expression $(C_3\text{-}C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3\text{-}C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable $(C_3\text{-}C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^2$ and $R^3$ radicals may each independently be substituted by one or more substituents selected from —$(C_1\text{-}C_{12})$-alkyl, —$(C_3\text{-}C_{12})$-cycloalkyl, —$(C_3\text{-}C_{12})$-heterocycloalkyl, —O—$(C_1\text{-}C_{12})$-alkyl, —O—$(C_1\text{-}C_{12})$-alkyl-$(C_6\text{-}C_{20})$-aryl, —O—$(C_3\text{-}C_{12})$-cycloalkyl, —S—$(C_1\text{-}C_{12})$-alkyl, —S—$(C_3\text{-}C_{12})$-cycloalkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl, —$(C_3\text{-}C_{20})$-heteroaryl, —$(C_3\text{-}C_{20})$-heteroaryl-$(C_1\text{-}C_{12})$-alkyl, —$(C_3\text{-}C_{20})$-heteroaryl-O—$(C_1\text{-}C_{12})$-alkyl, —COOH, —OH, —$SO_3H$, —$NH_2$, halogen.

In one embodiment, the $R^1$, $R^2$ and $R^3$ radicals may each independently be substituted by one or more substituents selected from —$(C_1\text{-}C_{12})$-alkyl, —$(C_3\text{-}C_{12})$-cycloalkyl, —O—$(C_1\text{-}C_{12})$-alkyl, —O—$(C_1\text{-}C_{12})$-akyl-$(C_6\text{-}C_{20})$-aryl, —O—$(C_3\text{-}C_{12})$-cycloalkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl.

In one embodiment, the radicals $R^1$, $R^2$ and $R^3$ may each independently be substituted by one or more substituents selected from —$(C_1\text{-}C_{12})$-alkyl, —$(C_3\text{-}C_{12})$-cycloalkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl.

In one embodiment, the radicals $R^1$, $R^2$ and $R^3$ may each independently be substituted by one or more substituents selected from —$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl.

In one embodiment, the radicals $R^1$, $R^2$ and $R^3$ are unsubstituted.

In one preferred embodiment, $R^1$ is selected from —$(C_1\text{-}C_{12})$-alkyl, —$(C_6\text{-}C_{20})$-aryl, —$(C_3\text{-}C_{12})$-cycloalkyl, —$(C_3\text{-}C_{20})$-heteroaryl.

In one particularly preferred embodiment, $R^1$ is selected from —$(C_1\text{-}C_{12})$-alkyl, —$(C_6\text{-}C_{20})$-aryl, —$(C_3\text{-}C_{12})$-cycloalkyl.

In one preferred embodiment, $R^2$ is selected from —$(C_3\text{-}C_{12})$-cycloalkyl, —$(C_6\text{-}C_{20})$-aryl or —$(C_3\text{-}C_{20})$-heteroaryl.

In one particularly preferred embodiment, $R^2$ is selected from —$(C_3\text{-}C_{12})$-cycoalkyl, —$(C_6\text{-}C_{20})$-aryl.

In one embodiment, $R^1$ and $R^2$, if these are —$(C_3\text{-}C_{20})$-heteroaryl, are selected from heteroaryl radicals having five to ten ring atoms, preferably five or six ring atoms.

In one embodiment, $R^1$ and $R^2$, if these are —$(C_3\text{-}C_{20})$-heteroaryl, are selected from heteroaryl radicals having six to ten ring atoms, preferably six ring atoms.

In one embodiment, $R^1$ and $R^2$, if these are —$(C_3\text{-}C_{20})$-heteroaryl, are selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, $R^1$ and $R^2$, if they are —$(C_3\text{-}C_{20})$-heteroaryl, are selected from furyl, thienyl, pyrrolyl, imidazolyl, pyridyl, pyrimidyl, indolyl; especially furyl and imidazolyl; where the heteroaryl radicals mentioned may be substituted as described above.

In one embodiment, $R^1$ and $R^2$, if they are —$(C_3\text{-}C_{20})$-heteroaryl, are selected from 2-furyl, 2-thienyl, 2-pyrrolyl, 2-imidazolyl, 2-pyridyl, 2-pyrimidyl, 2-indolyl; especially 2-furyl and 2-imidazolyl; where the heteroaryl radicals mentioned may be substituted as described above.

In one embodiment, $R^1$ is selected from —$(C_1\text{-}C_{12})$-alkyl, cyclohexyl, phenyl and furyl, preferably tert-butyl, cyclohexyl, phenyl and 2-furyl, where the radicals mentioned may be substituted as described above. Preferably $R^2$ is selected from tert-butyl, cyclohexyl, phenyl, o-tolyl and 2-furyl, where the radicals mentioned are not further substituted.

In one embodiment, $R^2$ is selected from cyclohexyl, phenyl, furyl and imidazolyl, preferably cyclohexyl, phenyl, 2-pyrimidyl and 2-imidazolyl, where the radicals mentioned may be substituted as described above. Preferably $R^2$ is selected from cyclohexyl, phenyl, o-tolyl, 2-furyl and N-methyl-imidazol-2-yl, where the radicals mentioned are not further substituted.

In one embodiment, $R^3$ is selected from heteroaryl radicals having five to ten ring atoms, preferably five or six ring atoms.

In one embodiment, $R^3$ is selected from heteroaryl radicals having six to ten ring atoms, preferably six ring atoms.

In one embodiment $R^3$ is selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, $R^3$ is selected from furyl, thienyl, pyrrolyl, imidazolyl, pyridyl, pyrimidyl, indolyl, where the heteroaryl radicals mentioned may be substituted as described above.

In one embodiment, $R^3$ is selected from 2-furyl, 2-thienyl, 2-pyrrolyl, 2-imidazolyl, 2-pyridyl, 2-pyrimidyl, 2-indolyl, where the heteroaryl radicals mentioned may be substituted as described above.

In one embodiment, $R^3$ is selected from 2-furyl, N-phenylpyrrol-2-yl, N-(2-methoxyphenyl)-pyrrol-2-yl, N-methylimidazol-2-yl, 2-pyridyl, N-phenylindol-2-yl, where the heteroaryl radicals mentioned may be substituted as described above.

In one particularly preferred embodiment, $R^3$ is pyrimidyl or imidazolyl, preferably 2-pyrimidyl and 2-imidazolyl, where the radicals mentioned may be substituted as described above. In particular, $R^3$ is 2-pyrimidyl or N-methylimidazol-2-yl, where the radicals mentioned are not further substituted.

In one embodiment, the monophosphine ligand is selected from compounds of one of the formulae (1), (2), (7) to (9) and (11) to (14):

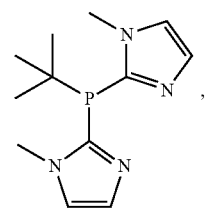
(1)

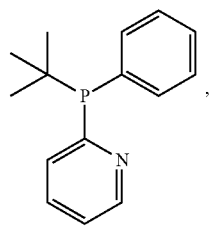
(2)

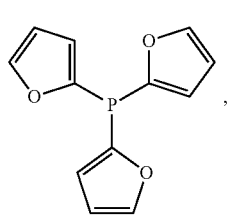
(7)

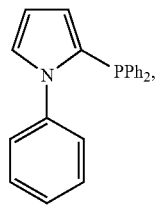
(8)

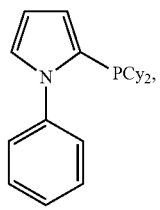
(9)

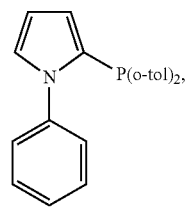
(11)

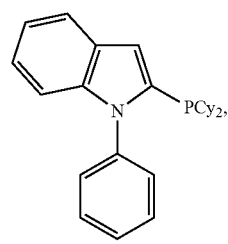
(12)

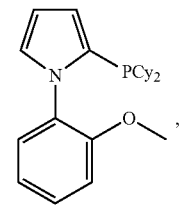
(13)

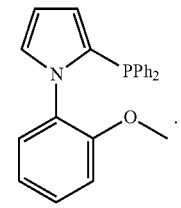
(14)

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 2 to 30 carbon atoms, preferably 6 to 22 carbon atoms, more preferably 8 to 12 carbon atoms, most preferably 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 12 carbon atoms, and most preferably 8 carbon atoms.

Suitable ethylenically unsaturated compounds are, for example:
ethene;
propene;
C4 olefins such as 1-butene, cis-2-butene, trans-2-butene, mixture of cis- and trans-2-butene, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadlene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins; triisobutene, tri-n-butene;
terpenes such as limonene, geraniol, farnesol, pinene, myrcene, carvone, 3-carene; polyunsaturated compounds having 18 carbon atoms, such as linoleic acid or linolenic acid; esters of unsaturated carboxylic acids, such as vinyl esters of acetic or propionic acid, alkyl esters of unsaturated carboxylic acids, methyl or ethyl esters of acrylic acid and methacrylic acid, oleic esters, such as methyl or ethyl oleate, esters of linoleic or linolenic acid; vinyl compounds such as vinyl acetate, vinylcyclohexene, styrene, alpha-methylstyrene, 2-isopropenylnaphthalene;
2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butene, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the Invention is catalysed by a Pd complex. The Pd complex may either be added in process step b) as a preformed complex comprising Pd and the monophosphine ligands or be formed in situ from a compound comprising Pd and the free monophosphine ligand. In this context, the compound comprising Pd is also referred to as catalyst precursor.

The preferred complexes may also comprise further ligands which coordinate to the metal atom. These are, for example, ethylenically unsaturated compounds or anions. Suitable additional ligands are, for example, styrene, acetate anions, maleimides (e.g. N-methyl-maleimide), 1,4-naphthoquinone, trifluoroacetate anions or chloride anions.

In the case that the catalyst is formed in situ, the ligand can be added in excess, such that the unbound ligand is also present in the reaction mixture.

In the case of the complex which is added right at the start as well, it is additionally possible to add further ligand, such that unbound ligand is also present in the reaction mixture.

In one variant, the compound comprising Pd is selected from palladium chloride ($PdCl_2$), palladium(II) acetylacetonate [$Pd(acac)_2$], palladium(II) acetate [$Pd(OAc)_2$], dichloro (1,5-cyclooctadiene)palladium(II) [$Pd(cod)_2Cl_2$], bis(dibenzylideneacetone)palladium [$Pd(dba)_2$], bis(acetonitrile) dichloropalladium(II) [$Pd(CH_3CN)_2Cl_2$], palladium (cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The aliphatic alcohol in process step c) may be branched or linear, cyclic, alicyclic or partly cyclic and is especially a $C_1$- to $C_{30}$-alkanol. It is possible to use monoalcohols or polyalcohols.

An aliphatic alcohol in the context of this invention refers to an alcohol which does not comprise any aromatic groups, i.e., for example, an alkanol, alkenol or alkynol.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, or silyl groups and/or halogen substituents.

In one embodiment, the alcohol does not comprise any further functional groups except for hydroxyl groups.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, 2-ethylhexanol, isononanol, 2-propyl-heptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, and mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxymethyl)ethane.

In one variant of the process, the alcohol in process step c) is selected from: sucrose, fructose, mannose, sorbose, galactose and glucose.

In a preferred embodiment of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 to 1:10, more preferably 1:3 to 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the monophosphine ligand to Pd is preferably between 0.1:1 and 400:1, preferably between 0.5:1 and 400:1, more preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have an acid strength of $pK_a \leq 5$, preferably an acid strength of $pK_a \leq 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

EXAMPLES

The examples which follow illustrate the invention.

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P} = SR_{1H} * (BF_{31P}/BF_{1H}) = SR_{1H} * 0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of chloro-2-pyridyl-tert-butylphosphine (Precursor A)

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 1: Synthesis of precursor A

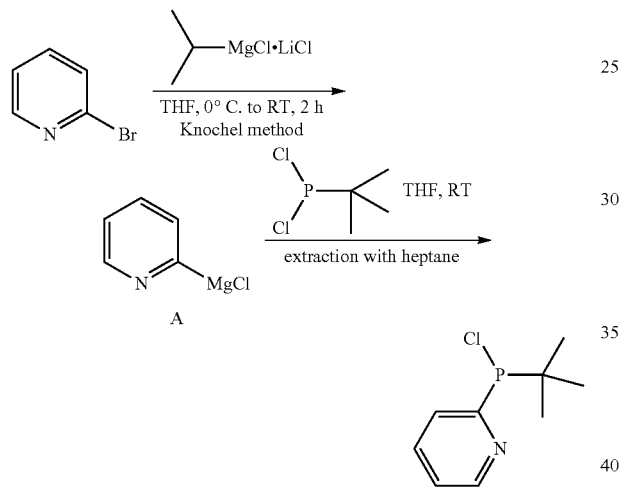

8.07 ml of a 1.3 M isopropylmagnesium chloride solution (Knochel's reagent) are introduced into a 50 ml round-bottom flask with magnetic stirrer and septum, and cooled to −15° C. Thereafter, 953.5 µl (10 mmol) of 2-bromopyridine are rapidly added dropwise. The solution immediately turns yellow. It is allowed to warm up to −10° C. The conversion of the reaction is determined as follows: about 100 µl solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution can be slowly added dropwise with a syringe pump to a solution of 1.748 g (11 mmol) of dichloro-tert-butylphosphine in 10 ml of THF which has been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight. According to GC-MS, a large amount of product has formed. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1$H NMR (300 MHz, $C_6D_6$): δ 8.36 (m, 1H, Py), 7.67 (m, 1H, Py), 7.03-6.93 (m, 1H, Py), 6.55-6.46 (m, 1H, Py), 1.07 (d, J=13.3 Hz, 9H, t-Bu).

$^{13}$C NMR (75 MHz, $C_6D_6$): δ 162.9, 162.6, 148.8, 135.5, 125.8, 125.7, 122.8, 35.3, 34.8, 25.9 and 25.8.

$^{31}$P NMR (121 MHz, $C_6D_6$) δ 97.9.

MS (EI) m:z (relative intensity) 201 (M$^+$,2), 147(32), 145 (100), 109 (17), 78 (8), 57.1 (17).

Preparation of Compound 1

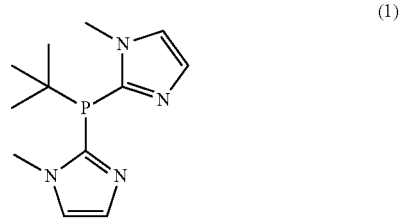 [SMILES: Cn1ccnc1P(c1nccn1C)C(C)(C)C]

(1)

0.78 g (9.5 mmol) of 1-methylimidazole are weighed out under argon in a 50 ml three-neck flask with thermometer and dropping funnel, and dissolved in 10 ml of THF. Then 1.6 ml of TMEDA are added to the solution. The mixture is then cooled down to −78° C. Thereafter 6 ml of 1,6 N n-butyllithium in hexane are added dropwise via dropping funnel. The 50 ml flask with the reaction mixture is stirred at room temperature for 30 minutes. Then 1.5 g of tert-butyldichlorophosphine are dissolved in 20 ml of THF. The 1-methylimidazole/BuLi mixture is then added dropwise at −78° C. to the tert-butyldichlorophosphine. This is followed by heating to room temperature. A product is precipitated. The suspension is filtered and the residue is dissolved in water and then washed three times with dichloromethane. The organic phase is dried over $Na_2SO_4$ and the solvent is then removed under reduced pressure. The residue is dissolved using 5 ml of dichloromethane and overlaid with 20 ml of diethyl ether. The product is crystallized. The product was obtained in 0.8 g.

Purity (NMR)=98%, $^{31}$P NMR ($CD_2Cl_2$, 121 MHz)=−32.25 ppm, $^{13}$C NMR ($CD_2Cl_2$, 75 MHz)=144 s, 130.2 d ($J_{PC}$=3.7 Hz), 123.8 s, 34.2 d, ($J_{PC}$=11.7 Hz), 25.9 d, ($J_{PC}$=14.3 Hz)

$^1$H NMR ($CD_2Cl_2$, 300 MHz,): 7.04, d, (J=1 Hz, 1H), 6.94 dd (J=1 Hz, J=1.5 Hz, 1H), 3.4 s (6H), 1.2 d (J=14.6 Hz, 9H)

HRMS: calculated for $C_{12}H_{19}N_4P$: 251.14201. found: 251.14206.

Preparation of 2-(tert-butyl(phenyl)phosphino)pyridine (Compound 2)

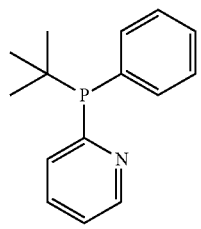
(2)

3.4 g (16.8 mmol) of 2-(tert-butylchlorophosphino)pyridine are dissolved under argon in 50 ml of absolute diethyl ether in a 100 ml three-neck flask equipped with low-temperature thermometer and magnetic stirrer. Cooling takes place to −78° C. At this temperature, over the course of 10 minutes, 10 ml of a 1.8 N phenyllithium solution (in dibutyl ether) are added by means of a dropping funnel. Stirring takes place at this temperature for 10 minutes, followed by warming to room temperature and stirring for a further half-hour. This solution is washed three times with 10 ml of degassed water. The organic phase is then distilled under a fine vacuum of $10^{-1}$ torr. Under this pressure, the product is obtained at 130° C. as a clear liquid in high purity of more than 97% (NMR). The yield is 3.85 g (93%).

Analysis:

$^{31}$P (acetone-$d_6$, 121 MHz), 16.31 s, $^{13}$C (75 MHz, acetone-$d_6$, 165.1 (d, $J_{PC}$=10.5 Hz), 150.3 (d, $J_{PC}$=5 Hz), 137.3 s, 137.0 s, 136.7 s, 135.9 d, 135.9 (d, $J_{PC}$=7.6 Hz), 131.1 s, 130.6 s, 130.2 s, 128.9 (d, $J_{PC}$=8 Hz), 122.9 s, 32.1 (d, $J_{PC}$=13.1 Hz), 28.5 (d, $J_{PC}$=13.7 Hz), $^1$H (acetone-$d_6$, 300 MHz):

8.74 (dm, J=4.7 Hz), 7.7-7.6 m (2 H), 7.4-7.3 (m, 3 H), 7.28-7.23 (m, 1 H), 1.2 (d, J=12.6 Hz, 9 H)

MS (EI, 70 eV): m/z (%), 243 (M+, 17), 203 (65), 187 (78), 156 (6), 126(8), 109(100), 78(11), 57(11), HRMS(EI), calculated for C15H18N1P1: 243.11714. found: 243.11753.

Further Ligands

The following compounds are commercially available and/or preparable by a known pathway.

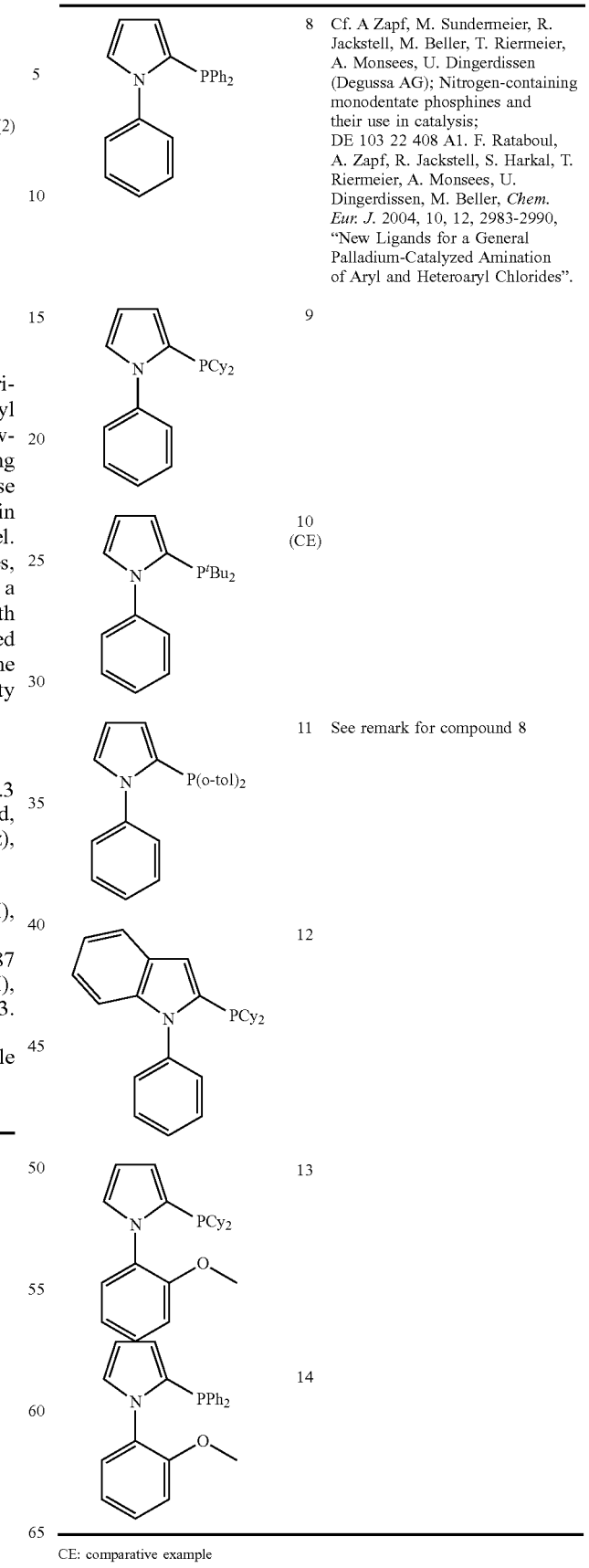

CE: comparative example

Alkoxycarbonylation Experiments
General Experiment Description for Reactions in Batchwise Mode The appropriate amounts of substrate, palladium salt, acid and alcohol are mixed under argon in a 50 ml Schlenk vessel while stirring with a magnetic stirrer.

A 100 ml steel autoclave from Parr provided with a gas inlet and a gas outlet valve, a digital pressure transducer, a temperature sensor and a ball valve, and an installed capillary for sampling, is freed of oxygen by means of vacuum and argon purging three times. Subsequently, the reaction solution from the Schlenk vessel is introduced by means of a capillary into the autoclave in an argon counterflow through the ball valve. Subsequently, either the appropriate amount of CO is injected at room temperature and then the autoclave is heated up to reaction temperature (reactions that are not run under constant pressure) or the autoclave is first heated up to reaction temperature and then the CO is injected by means of a burette connected to the autoclave by means of a pressure reducer. This burette is then filled with CO to about 100 bar and, during the reaction, supplies the CO required at a constant pressure. This burette has a dead volume of about 30 ml and is provided with a digital pressure transducer. Then the reaction is conducted at the required temperature for the required time while stirring. In the course of this, by means of software (Specview from SpecView Corporation) and a Parr 4870 process controller and a 4875 power controller, data for the pressure variation in the autoclave and in the gas burette are recorded. If required, via the capillary, the GC samples are collected and analysed. For this purpose, a suitable exact amount (2-10 ml) of isooctane as internal standard is also added to the Schlenk vessel before the reaction. These also give information about the course of the reaction. At the end of the reaction, the autoclave is cooled down to room temperature, the pressure is cautiously released, isooctane is added if necessary as internal standard, and a GC analysis or, in the case of new products, a GC-MS analysis is conducted.

General Experimental Method for Autoclave Experiments in Glass Vials

A 300 ml Parr reactor is used. Matched to this is an aluminium block of corresponding dimensions which has been manufactured in-house and which is suitable for heating by means of a conventional magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and these are transferred into the autoclave under argon. The autoclave is purged with CO and filled at room temperature with the CO pressure intended. Then, by means of the magnetic stirrer, under magnetic stirring, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which are used to determine yields and selectivities.

Analysis:
Methanol Analysis

Methanol was pretreated in a solvent drying unit: Pure Solv MD-/Solvent purification system, Innovative Technology Inc. One Industrial Way, Amesbury MA 01013

Water Values:

Determined by Karl Fischer Titration: TitraLab 580-TIM580, Radiometer Analytical SAS (Karl-Fischer Titration), water content: measuring ranges, 0.1-100% w/w, measured water content: 0.13889%

The following were used:

Technical methanol Applichem: No. A2954,5000, batch number LOT: 3L005446 water content max. 1%

Methanol Acros Organics (over molecular sieve): water content 0.005%, code number: 364390010, batch number: LOT 1370321

Methoxycarbonylation of Ethene

A 50 ml Schlenk vessel was charged with $Pd(acac)_2$ (6.53 mg, 0.04 mol %), ligand (0.16 mol %), ethene (1.5 g, 53 mmol), 20 ml of methanol and para-toluenesulphonic acid (PTSA, 61 mg, 0.6 mol %). The reaction mixture was transferred by means of a capillary in an argon counter-current into a 100 ml steel autoclave as described above. The CO pressure was adjusted to 40 bar. The reaction ran at 80° C. for 3 hours. After the end of the reaction, the autoclave was cooled to room temperature and cautiously decompressed. Isooctane (100 µl) was added as internal GC standard. Yield and regioselectivity were determined by means of GC.

The results are shown in the table below.

| Ligand  | Yield |
|---------|-------|
| 1       | 30%   |
| 2       | 14%   |
| 3 (CE)  | 3%    |
| 7       | 18%   |
| 10 (CE) | 0%    |

CE: comparative example

The ligands 1, 2 and 7 according to the invention achieve much better yields in the methoxycarbonylation of ethene than do the comparative ligands 3 and 10.

Isomerizing Regioselective Methoxycarbonylation of 1-octene

Scheme 8: Regioselective methoxycarbonylation of 1-octene; the reaction, in addition to the terminal methoxycarbonylation, leads primarily to a secondary reaction in 2-position (identified as major).

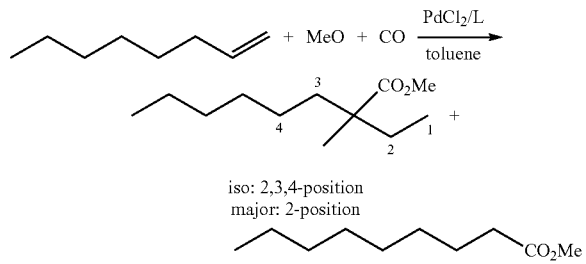

iso: 2,3,4-position
major: 2-position

The iso/n ratio reported below indicates the ratio of olefins reacted internally to form esters to olefins reacted terminally to form esters.

Variant a)

A 4 ml vial was charged with PdCl$_2$ (1.77 mg, 1.0 mol %) and ligand (4.0 mol %) and a magnetic stirrer bar was added. Then toluene (2 ml), 1-octene (157 µl, 1 mmol) and MeOH (40.5 µl, 1 mmol) were injected via a syringe. The vial was placed on a sample holder, which was inserted in turn under argon atmosphere into a 300 ml Parr autoclave. After threefold purging of the autoclave with nitrogen, the CO pressure was adjusted to 40 bar. The reaction ran at 120° C. for 20 hours. After the end of the reaction, the autoclave was cooled to room temperature and cautiously decompressed. Isooctane (100 µl) was added as internal GC standard. Yield and regioselectivity were determined by means of GC.

The results are shown in the table below.

| Ligand | Yield | iso/n |
|---|---|---|
| 2 | 75% | 28/72 |
| 3 (CE) | 87% | 55/45 |
| 8 | 66% | 36/64 |
| 9 | 49% | 79/21 |
| 10 (CE) | 10% | 45/55 |
| 11 | 30% | 75/25 |
| 12 | 49% | 82/18 |
| 13 | 74% | 86/14 |
| 14 | 22% | 90/10 |

CE: comparative example

The ligands according to the invention are notable for high yields and either high iso/n selectivity (ligands 9, 11 to 14) or high n/iso selectivity (ligands 2 and 8). Conversely, the prior-art ligand 10 achieves only a low yield and, furthermore, is not regioselective. Comparative ligand 3 does achieve a high yield, but is likewise not regioselective.

Variant b)

A 25 ml Schlenk vessel was charged with [Pd(acac)$_2$] (1.95 mg, 0.04 mol %), p-toluenesulphonic acid (PTSA) (18.24 µl, 0.6 mol %) and MeOH (10 ml). A 4 ml vial was charged with the ligand (0.16 mol %), and a magnetic stirrer bar was added. Thereafter, 1.25 ml of the clear yellow solution from the Schlenk vessel and 1-octene (315 µl, 2 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (100 µl) was added as internal GC standard. Yield and regioselectivity were determined by means of GC.

The results are shown in the table below.

| Ligand | Yield | iso/n |
|---|---|---|
| 2 | 26% | 74/26 |
| 3 (CE) | 16% | 77/23 |
| 7 | 20% | 74/26 |
| 10 (CE) | 0% | N/A |

CE: comparative example

Here again, the ligands 2 and 7 of the invention exhibit a high iso/n selectivity and a higher yield than the comparative ligands 3 and 10.

The invention claimed is:

1. A regioselective process for preparing an ester comprising the following process steps:
   a) introducing an ethylenieally unsaturated compound having 8 to 12 carbon atoms, forming a reaction mixture;
   b) adding a monophosphine ligand and a compound which comprises Pd, or adding a complex comprising Pd and a monophosphine ligand;
   c) adding an aliphatic alcohol;
   d) supplying CO;
   e) heating the reaction mixture, the ethylenically unsaturated compound being reacted with the epithelium CO and aliphatic alcohol to form the ester; where the monophosphine ligand is

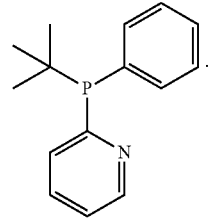

(2)

2. The process according to claim 1, wherein the ethylenically unsaturated compound is selected from the group consisting of ethene, propene, 1-butene, 2-butene, isobutene, 1,3-butadiene, 1-pentene, 2-pentene, 2-methyl-1-butene, 3-methyl-1-butene, 2-methyl-2-butene, hexene, tetramethylethylene, heptene, 1-octene, 2-octene, di-n-butene, and mixtures thereof.

3. The process according to claim 1, wherein the compound comprising Pd in process step b) is selected from the group consisting of palladium dichloride, palladium(II) acetylacetonate, palladium(II) acetate, dichloro(1,5-cyclooctadiene)palladium(II), bis(dibenzylideneacetone)palladium, bis(acetonitrile)dichloro-palladium(II), and palladium (cinnamyl) dichloride.

4. The process according to claim 1, wherein the alcohol in process step c) is selected from the group consisting of methanol, ethanol, 1-propanol, 1-butanol, 1-pentanol, 1-hexanol, 2-propanol, tert-butanol, 3-pentanol, cyclohexanol, and mixtures thereof.

5. The process according to claim 1, wherein the alcohol in process step c) is selected from the group consisting of methanol and ethanol.

* * * * *